(12) United States Patent
Hanan et al.

(10) Patent No.: US 8,225,667 B2
(45) Date of Patent: Jul. 24, 2012

(54) CONTINUOUS AUTONOMOUS TESTER

(75) Inventors: Jay Hanan, Sand Springs, OK (US); Walter Matulewicz, Broken Arrow, OK (US)

(73) Assignee: Veracity Technology Solutions, LLC, Midwest City, OK (US)

( * ) Notice: Subject to any disclaimer, the term of this patent is extended or adjusted under 35 U.S.C. 154(b) by 423 days.

(21) Appl. No.: 12/431,697

(22) Filed: Apr. 28, 2009

(65) Prior Publication Data

US 2010/0011864 A1 Jan. 21, 2010

Related U.S. Application Data

(60) Provisional application No. 61/048,349, filed on Apr. 28, 2008.

(51) Int. Cl.
*G01N 9/24* (2006.01)
*G01N 29/04* (2006.01)

(52) U.S. Cl. ............... 73/619; 73/584; 73/618; 73/620
(58) Field of Classification Search ............... 73/620, 73/634
See application file for complete search history.

(56) References Cited

U.S. PATENT DOCUMENTS

| 6,220,099 B1* | 4/2001 | Marti et al. ............ 73/633 |
| 7,372,247 B1* | 5/2008 | Giusti et al. ............ 324/67 |
| 2005/0113975 A1* | 5/2005 | Seemann ............ 700/245 |
| 2007/0156286 A1* | 7/2007 | Yamauchi ............ 700/245 |

* cited by examiner

*Primary Examiner* — Lisa Caputo
*Assistant Examiner* — Roger Hernandez-Prewitt
(74) *Attorney, Agent, or Firm* — Tomlinson Rust McKinstry Grable

(57) ABSTRACT

A self propelled scanning device is disclosed. The device includes a self propelled chassis that is locomotive across a surface to be scanned, a translator attached to the chassis, and a carriage attached to the translator and adapted to receive a scanner. The translator selectively moves the carriage in at least one dimension across the surface to be scanned.

16 Claims, 4 Drawing Sheets

CONTINUOUS AUTONOMOUS TESTER

CROSS REFERENCE TO RELATED APPLICATIONS

This application claims the priority of U.S. Provisional Patent Application No. 61/048,349 entitled "CONTINUOUS AUTONOMOUS TESTER," filed Apr. 28, 2008, the contents of which are hereby incorporated by reference.

FIELD OF THE INVENTION

This disclosure relates to ultrasonic testing in general and, more specifically, to automated ultrasonic testing.

BACKGROUND OF THE INVENTION

As an aircraft ages, it becomes necessary to perform non-destructive testing on various exterior surfaces of the aircraft. This is a Federal Aviation Administration (FAA) requirement that ensures continued airworthiness. Presently, this is a labor intensive process that requires a mechanic to traverse the specified section of the aircraft with a hand held ultra sonic device. Minor fluctuations in pressure on the device or slippage can cause inaccurate readings that require a second scan. It will be appreciated that similar problems arise in testing of other structures.

Examples of automated non-destructive testing have been demonstrated. However, they are restrictive in that a frame or other form of external reference is needed to identify the location of the fasteners for the sensors.

What is needed is a system and method that addressees the above, and related, issues.

SUMMARY OF THE INVENTION

The invention disclosed and claimed herein, in one aspect thereof, comprises a self propelled scanning device. The device includes a self propelled chassis that is locomotive across a surface to be scanned, a translator attached to the chassis, and a carriage attached to the translator and adapted to receive a scanner. The translator selectively moves the carriage in at least one dimension across the surface to be scanned.

In some embodiments, the self propelled chassis provides a pair of slip resistant tracks in contact with the surface to be scanned, for providing locomotion across the surface. The self propelled chassis may provide a platform for a portable control computer. The device may include the portable control computer secured to the chassis and configured to selectively control the movement of the chassis on the surface to be scanned. The control computer may also control the translation of the carriage on the translator.

In some embodiments, the carriage is attached to the translator by a shock dampening suspension. The shock dampening suspension may comprise a coil-over-shock suspension. The carriage may have at least one rolling caster interposing the surface to be scanned and the carriage. The carriage may be configured to pivot about an axis orthogonal to a direction of translation.

The invention disclosed and claimed herein, in another aspect thereof, comprises an automated wing scanning device for operation upon an upper surface of an aircraft wing having a surface skin with a plurality of fasteners thereon connecting the skin to an airframe. The device has a track propelled chassis, the tracks having rubber treads and a sufficient base area to allow the chassis to operate on a slope of up to at least fifteen degrees when the surface skin is wet. A translation table is connected to the chassis and provides a suspended carriage that is selectively rastered across the surface skin. An ultrasonic scanner is secured within the suspended carriage for selectively scanning the wing surface. A control system controls the chassis to follow a predetermined scan path across the wing surface, controls the translation table to translate the carriage and scanner across the wing surface, and accepts readings from the ultrasonic scanner. The device may also comprise a camera mounted to the chassis with a view of the wing surface and interfaced to the control system to allow the control system to correct deviations from the predetermined path on the wing surface.

DETAILED DESCRIPTION OF THE PREFERRED EMBODIMENTS

Figure 1:
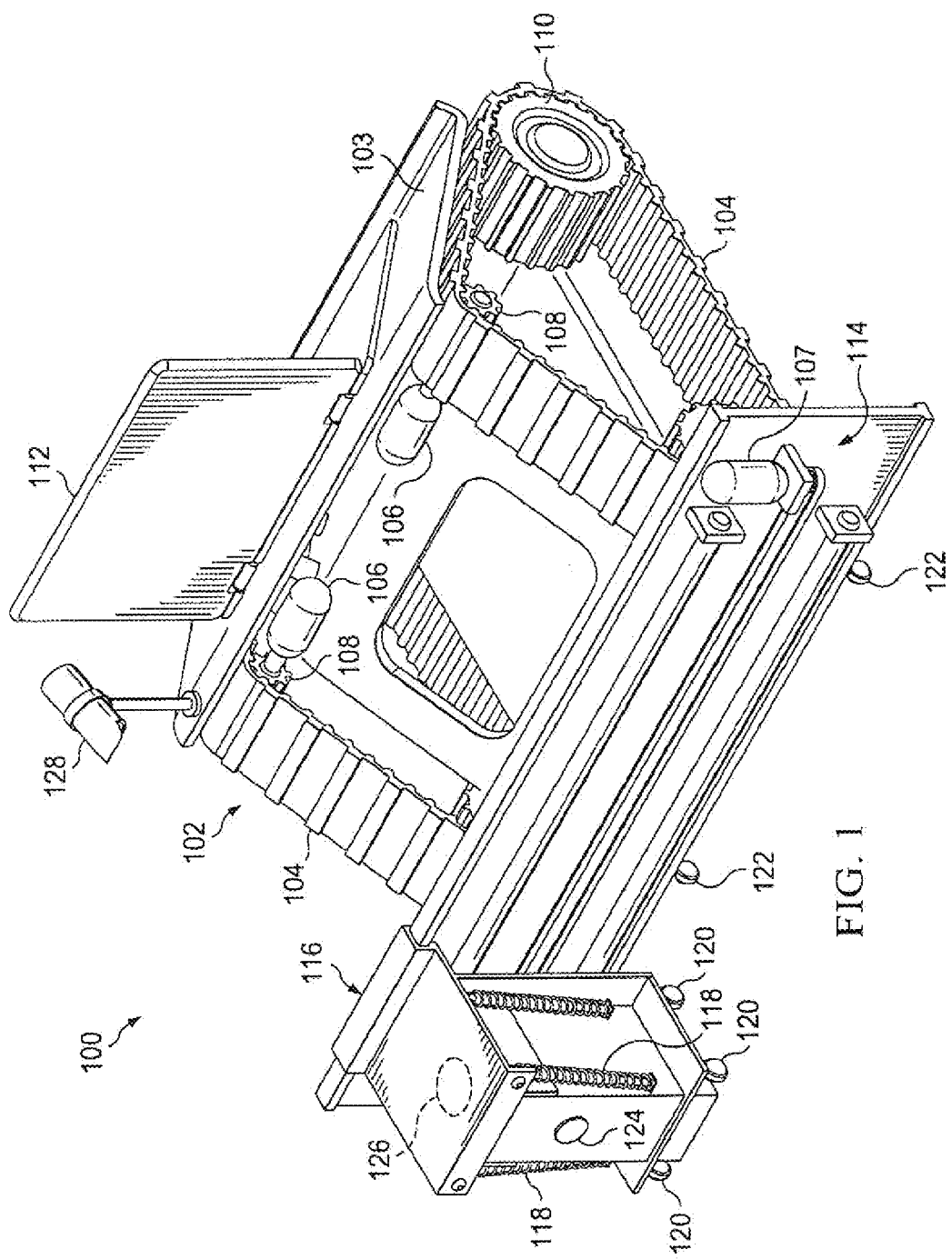
FIG. 1 is perspective view of one embodiment of an autonomous tester according to the present disclosure.

Referring now to FIG. 1, a perspective view of one embodiment of an autonomous tester according to the present disclosure is shown. The autonomous tester 100 in the present embodiment is a robotic design intended to perform ultrasonic testing on the wing of an aircraft. As will be described herein, the autonomous tester 100 will be able to complete ultrasonic testing of fasteners along the surface of an aircraft with minimal user input. The autonomous tester 100 is generally of a modular design to allow easy replacement and upgrade of components.

One of the major components of the tester 100 is the robotic chassis 102. One function of the chassis 102 is to provide a base upon which the remaining components may be attached. The chassis may be constructed of lightweight metals or alloys that are sufficiently strong and lightweight enough to allow the chassis to carry the various additional components of the tester 100. In one embodiment, the completed tester 100 will be movable by a single person.

In the present embodiment, the chassis is of a tracked design, having two tracks 104. The tracked design allows the tester 100 to have complete freedom of movement across two dimensions. Where design constraints allow, the tester 100 could be equipped with wheels or other locomotion devices. The tracks 104 may be rubber, rubber coated, or equipped with rubber pads to allow the tester 100 to operate with sure footedness across various surfaces. In some forms of ultrasonic testing, the surface upon which the tester 100 operates will be wet and therefore slick. Since aircraft wings are seldom perfectly level, the tester 100 also is required to be able to operate on varying slopes. In some embodiments, the tester 100 will be required to operate on slopes of up to 15 degrees, and the present design has been found to exceed this threshold.

In the present embodiment, the power for the locomotion of the tester 100 is provided by a pair of electric motors 106. As can be seen, the electric motors 106 will interact with the tracks 104 by a pair of sprockets 108. In other embodiments, other devices may be used to transfer torque from the motors 106 to the tracks 104.

In one embodiment, a pair of sprockets 110 (only one visible in the present view) will be provided near the base of the tracks 104, creating a triangular configuration on each side of the chassis 102. This configuration will allow the motors 106 to be away from the base of the chassis 102 while giving the tracks 104 an increased amount of stability. In other embodiments, a traditional track configuration (e.g., non-triangular) may be used. It is understood that various idlers and shock absorbers may be part of the track system. This will allow the tracks to contour to the surface being scanned, enhancing the stability of the tester 100.

The chassis 102 may also have a platform 103 for mounting a control computer 112. In the present embodiment, the control computer 112 is a personal laptop computer, but in other embodiments, the control computer could be built into the body of the chassis 102 and could be a purpose-built machine. As will be explained in greater detail below, the control computer 112 will control the operation of the electric motors 106 and thus the speed and direction of the tester 100. The various motors of the present disclosure may be open loop AC or DC motors, stepper motors, servo motors, or other motors that satisfy the particular application. In one embodiment, the tester 100 will have a maximum forward speed of about 1 inches per second. This maximum speed may be the same in reverse, although it is understood that, in operation the tester 100 may not travel this fast.

The tester 100 may also provide a translation table 114. The translation table 114 provides for movement (e.g., translation or rastering) of a carriage 116 in a direction lateral to the direction of travel of the tester 100. In the present embodiment, the translation table 114 is belt driven and electrically powered by a motor 107.

The attachment point between the translation table 114 and the chassis 102 may also provide a pivot point, allowing self adjustment of the slope of the translation table 114 to account for uneven surfaces on the scanned surface.

The carriage 116 may provide a suspension system which may comprise a set of coil over shocks 118. An ultrasonic sensor (shown as 206 in FIG. 2) may be carried in the carriage 116 and the suspension system will allow the sensor to remain the appropriate distance from the surface being scanned while also absorbing impact. Ball casters 120 may also be provided on the carriage 116 to aid in keeping the ultrasonic sensor held in the appropriate location. In another embodiment, a combination lens and bumper, possibly made from a polymer, may be provided instead of, or in addition to, the ball casters 120. The use of a lens may also focus ultrasonic energy and enhance scanning. Ball casters 122 may be provided at various points along the translation table 114 to aid in allowing the translation table 114 to self rotate to follow contours of the scanned surface. In other embodiments, various replaceable bumpers may be used in place of the ball casters 122.

The carriage 116, in addition to securing the scanner, may provide for power and/or data cables to reach to and interface with the scanner. In the present embodiment, this is accomplished via a port or opening 124 in the carriage 116. Another possible location 126 for the port is shown in dotted line.

As will be described more fully below, the tester 100 may also be equipped with a camera 128 used for tracking the progress of the tester 100 along the testing surface. The camera 128 is shown in the present embodiment mounted on the platform 103, but it is understood that the camera 128 may be located in a number of locations on the chassis 102 and still be able to capture images or moving pictures of the surface.

Figure 2:
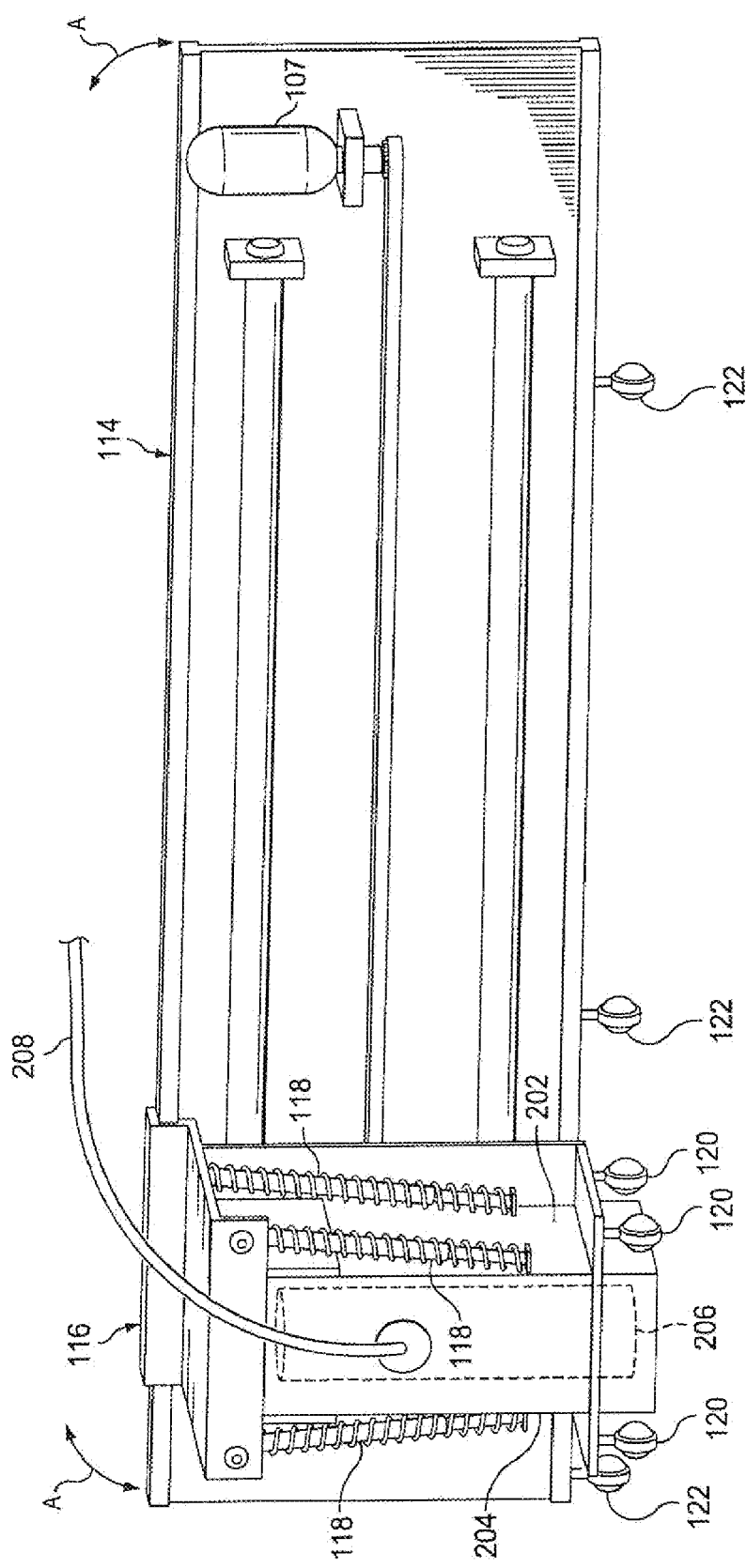
FIG. 2 is a frontal view of a translation table and ultrasonic transducer of the autonomous tester of FIG. 1.

Referring now to FIG. 2, a frontal view of a translation table and ultrasonic transducer of the autonomous tester of FIG. 1 is shown. From the viewpoint of FIG. 2, it can be seen that the translation table 114 of the present embodiment provides two ball casters 122 as previously described. In the present embodiment, the translation table 114 provides a rail-mounted, motor-driven system for moving the carriage 116 in a lateral direction for scanning purposes. However, it is understood that, in other embodiments, other types of translation tables may be used. Additionally, in some embodiments, an array of carriages 116 may be utilized, each containing an ultrasonic scanner. In such an embodiment, the carriages would be arrayed across the front of the chassis 102, obviating the need for a translation table to move a single carriage 116 in a lateral direction for scanning.

In addition to translating the carriage 116 and scanner 206 laterally, the arrows A indicate how the translation table itself may be allowed to rotate or tilt. This may be accomplished in the manner in which the translation table 114 is mounted to the chassis 102. For example, a rotating mount using a ball bearing or sleeve bearing could be utilized.

From the viewpoint of FIG. 2, it can be seen that in the present embodiment, the carriage 116 comprises an outer carriage 202 and an inner carriage 204. The carriage 116 is designed to allow displacement of the inner carriage 204 into the outer carriage 202. This configuration works in conjunction with the coil over shocks 118 to properly suspend a scanner 206 (shown in dotted line) over, or in contact with, the surface to be scanned. It is understood that, in other embodiments, the scanner 206 may be properly located relative to the surface by other configurations.

In one embodiment, the scanner 206 is a phased array ultrasonic transducer (PAUT) from Ultrasonix. Data from the ultrasonic scanner 206 may be provided to a computer by a data link 208. This may be a serial connection, a universal serial bus (USB) connection or another type of connection with sufficient bandwidth and durability.

Figure 3:
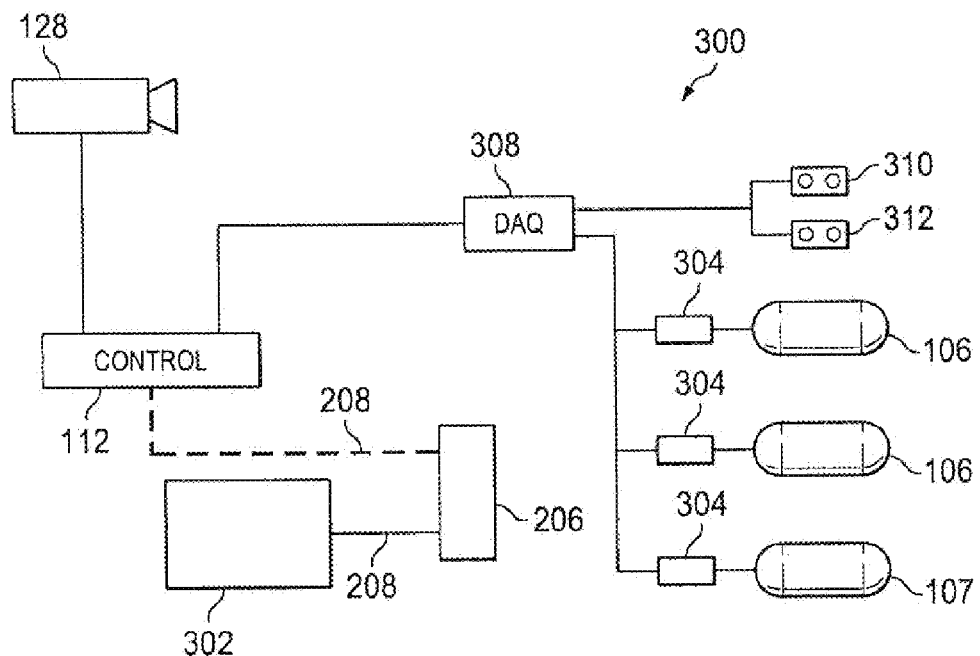
FIG. 3 is a schematic diagram of the control system of the autonomous tester of FIG. 1.

Referring now to FIG. 3, a schematic diagram of the control system of the autonomous tester of FIG. 1 is shown. Here, one possible way of connecting the control computer to the various components of the tester 100 is shown. As previously described, the control computer 112 may be a personal computer or could also be a purpose-built computer designed specifically to operate the tester 100. The control computer may interact with the various other components of the scanner 100 in a variety of ways. In one embodiment, the control computer 112 will be running the commercially available control software LabView.

The control computer 112 may interface directly with the camera 128. The camera 128 may connect to the control computer 112 via a universal serial bus (USB) cable or an IEEE 1394 (Firewire) connection. Implemented in the control computer 112 may be an algorithm that accepts images from the camera 128 of the surface being scanned and uses such images to correct for displacement errors when the scanner 100 is scanning a surface. Additionally, some embodiments of the tester 100 may provide for data gathering by the camera 128 instead of, or in addition to, the ultrasonic scanner 206. In some applications, the camera may be utilized to capture video or composite still images that may be used for evaluation of the surface being scanned.

In one embodiment, the control computer 112 may interface with data acquisition (DAQ) hardware 308. In one example, the DAQ 308 is a USB DAQ 6216 from National Instruments. This device is powered via a USB connection with the control computer 112. The DAQ 308 provides a way for the control computer 112 to control the motors 106, 107 as well as obtain information back form the motors that can be used to determine the distance traveled or rotated by the tester 100. In some embodiments, various other sensors can be connected through the DAQ 308, such as the optional IR sensors 310, 312 that may be mounted to the tester 100 to determine, for example, when the tester 100 has neared the edge of a surface or other obstacle.

The DAQ 308 may interact with the motors 106, 107 through one or more drive boards 304. The drive boards 304 may be connected to a power supply (not shown) to deliver a predetermined amount of power to the motors 106, 107 based on one or more control signals from the DAQ 308. In one embodiment, the drive boards are Syren 25 devices from Dimension Engineering. In other embodiments, other devices, such as electronic speed controllers, could be used to provide power to the boards based on control signals from the DAQ 308 and/or control computer 112.

In the present embodiment, the ultrasonic scanner 206 interacts with a separate scan computer 302 that powers the scanner 206 and collects the scan data as well. The scan computer may be located remotely and connected to the scanner 206 by the data link 208. In cases where the scan computer 302 is located remotely from the tester 100, the scan computer 302 may interface with the control computer 112 to provide start and stop sequences and other data to the control computer. This allows the scan computer to operate as a remote control for the tester 100. In other embodiments, the scan computer is located on the tester 100. In some embodiments, the control computer 112 will accept scan data from the scanner 206, obviating the need for the scan computer. In this case, the data link 208 will connect directly to the control computer 112 as shown in dotted line.

Figure 4:
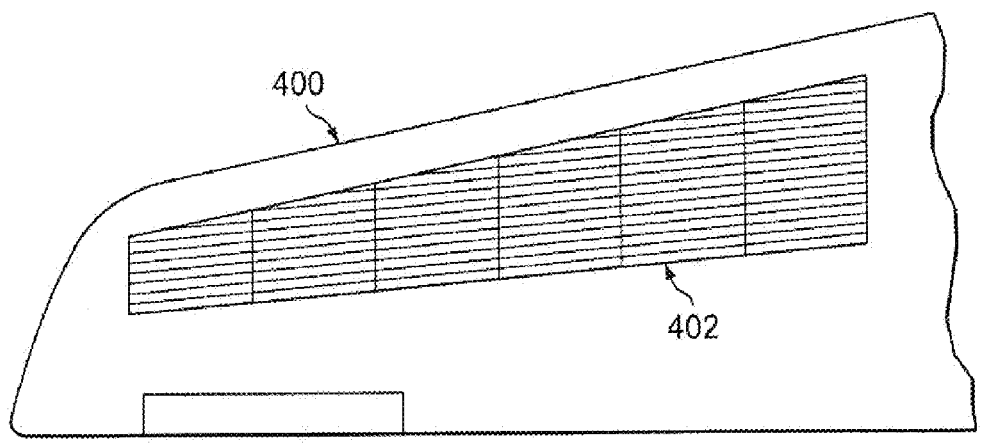
FIG. 4 is a superior view of portion of an aircraft wing upon which various embodiments of the autonomous tester of the present disclosure may operate.

Referring now to FIG. 4, a superior view of a portion of an aircraft wing upon which various embodiments of the autonomous tester of the present disclosure may operate is shown. It is understood that the tester 100 of the present disclosure is described in an exemplary fashion as being utilized to scan the surface, particularly the fasteners, on an aircraft wing. However, it is also understood that the various embodiments of the tester 100 of the present disclosure may be readily utilized or adapted to scan or test many surfaces, whether on an aircraft or otherwise. Moreover, even when utilized in the context of an aircraft wing, the tester 100 may test for corrosion and other defects whether they occur on or near a fastener or otherwise.

The aircraft wing 400 may comprise an airframe or skeleton covered by an aircraft skin or skins. The skin may be lightweight aluminum or other materials having sufficient strength to withstand the aerodynamic forces of flight, yet lightweight enough to actually be used on an aircraft. In order to function properly, the various skins covering the airframe may be fastened to the airframe with hundreds or thousands of discrete fasteners. In some cases, these fasteners will be placed in an orderly fashion corresponding to the underlying airframe. The grid 402 is illustrative of one possible fastener pattern on a portion of the wing 400.

Figure 5:
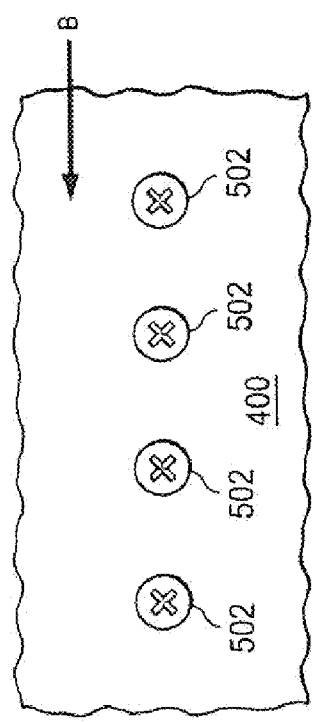
FIG. 5 is a close up superior view of a portion of an aircraft wing illustrating skin fasteners.

Referring now also to FIG. 5, a close up superior view of a portion of the aircraft wing 400 is shown. Here, it can be seen that along each line of the grid 402 may be a plurality of fasteners 502. These fasteners may proceed from the outside of the aircraft wing through the skin 400 and into the airframe. It is these discrete fasteners which may be scanned by the tester 100 of the present disclosure. A line B is shown to indicate a direction of travel for the tester. As the test progresses, an ultrasonic scan may be taken of each fastener 502 and possibly the surrounding area. The translation table 114 may be used to move the scanner 206 to an adjacent row of fasteners. The translation table 114 allows the scanner to scan an entire area of fasteners as the tester moves rather than limiting the tester to a single row of fasteners per pass. As previously described, an array of scanners could also be utilized in this regard and translation or rastering may not be needed.

Figure 6:
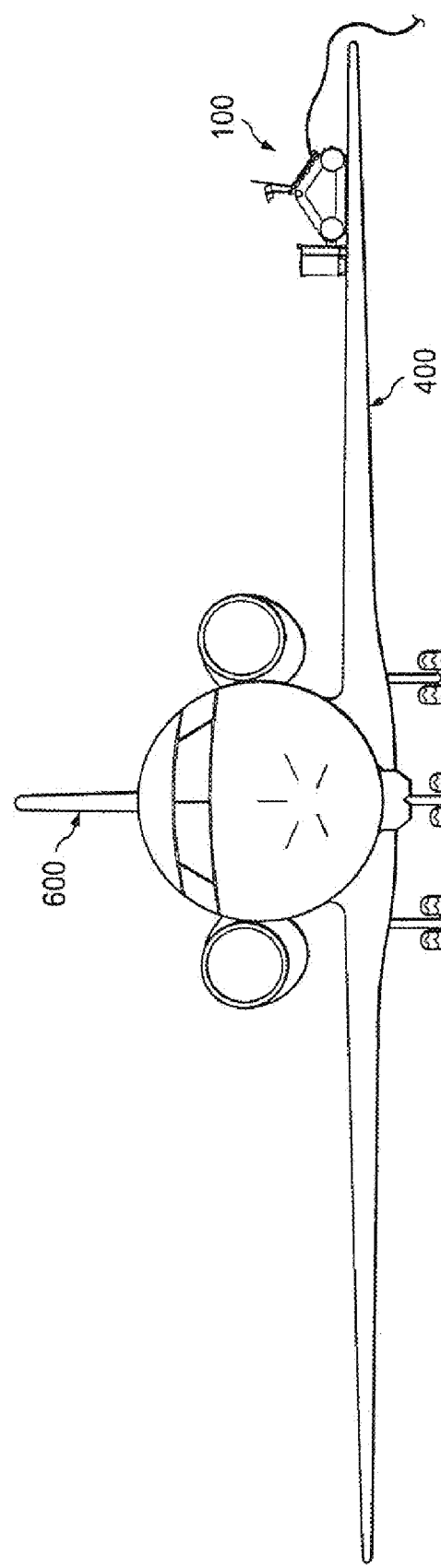
FIG. 6 is a perspective view of an aircraft wing with one embodiment of an autonomous tester of the present disclosure operating a testing sequence thereon.

Referring now also to FIG. 6, a perspective view of an aircraft wing with an autonomous tester 100 in a starting position is shown. A user of the scanner 100 may be prompted to enter wing specifications (e.g., on the control computer) that may include horizontal distance and a width to be traveled by the tester 100 after being placed on the wing 400. After entering scanning details by the user, the tester 100 may travel forward the distance specified by the user, pausing at a user-specified scan distance so that the translation table may move the carriage 116 and consequently the scanner 206 to the appropriate location over the correct fastener. The control computer 112 will collect scans and may be able to build a damage map of the wing fasteners in a manner similar to that seen in C-scans.

Because the surface of the wing 400 may not be level and may be wet, errors may occur in the travel of the tester 100 that cannot be compensated for merely by adjustments of the carriage on the translation table 114. These errors may be detected by the onboard camera, based on captured images of the fasteners and other wing features as the tester 100 moves along the wing surface. This information may be utilized by the control computer 112 to correct the path of the tester 100 by controlling the electric motors 106 that provide power to the tracks 104.

For visual tracking, various algorithms could be utilized, such as a neural network algorithm. This may be utilized in conjunction with image capture to allow the computer to learn the features of the aircraft wing as the tester progresses. As features are identified moving into the field of view of the camera 128, they may be tracked across the field of view as the tester 100 progresses. The computer 112 may determine an incorrect displacement of features across the camera's field of view to determine if the tester 100 is beginning to veer off course. This information can then be utilized by the control computer 112 to determine a course correction for the tester 100.

In one possible neural network suitable for guiding the tester 100, gradient based features are extracted from targets and non-targets for input to the neural network. The gradient features are sensitive to edge and texture information.

The objective is to automatically assign initial targets based on features and allow the tester 100 to traverse over them autonomously. In one embodiment, targets are selected while the translation table 114 is active (tester 100 is paused). However, real-time tracking and 30 fps video from the camera 128 allows automated selection of targets at speed. Due to slipping or uneven wing surfaces, the tester 100 may need to correct steering while moving the prescribed distance. Additionally, small corrections may be implemented in the scanner software accounting for minor overlap between ultrasonic scans. Targets, such as fasteners, vary in terms of texture, contrast, sharpness of edge, and size.

Various feature extractors exhibit tradeoffs in terms of sensitivity and processing requirements as related to the characteristics of candidate target classes. Each target may be processed by a feature extractor selected for optimal representation in the neural network. Optimal feature selection can be automated by observing features over multiple frames.

The vision software may also facilitate the recognition of locations being scanned in an absolute coordinate system. For example, within a test section on an aircraft panel, a particular position may have unique characteristics typically associated with fastener positions. These characteristics can be used by a neural network or other similar software to provide a positional reference in translation and rotation for the camera with respect to the panel. Such recognition can be calibrated. Hence, it becomes unnecessary to measure by hand the starting position of the robot connected to the camera. Such global position sensitivity can be trained for specific airframes.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A self propelled scanning device comprising:
   a self propelled chassis being locomotive across a surface to be scanned;
   a translator attached to the chassis; and
   a carriage attached to the translator and adapted to receive a scanner;
   wherein the translator selectively moves the carriage in at least one dimension across the surface to be scanned;
   wherein the carriage is attached to the translator by a self leveling suspension;
   wherein a shock dampening suspension comprises a coil-over-shock suspension; and
   wherein the carriage has at least one rolling caster interposing the surface to be scanned and the carriage.

2. The device of claim 1, wherein the self propelled chassis provides a pair of slip resistant tracks in contact with the surface to be scanned, for providing locomotion across the surface.

3. The device of claim 1, wherein the self propelled chassis provides a platform for a portable control computer.

4. The device of claim 1, further comprising a portable control computer secured to the chassis and configured to selectively control the movement of the chassis on the surface to be scanned.

5. The device of claim 4, wherein the portable control computer controls the translation of the carriage on the translator.

6. The device of claim 1, wherein the carriage is configured to pivot about an axis orthogonal to a direction of translation.

7. The device of claim 1, further comprising:
   a control computer; and
   a vision system mounted to the chassis and having at least one camera directed to the surface;
   wherein the vision system detects displacement errors in the path of the chassis that are corrected by the control computer.

8. A device for automated scanning of a surface comprising:
   a self propelled and steerable chassis;
   an ultrasonic scanning mechanism attached to the chassis;
   a control computer that controls the chassis to move along a predetermined route on the surface; and;
   wherein the ultrasonic scanning mechanism comprises an ultrasonic scanner on a translation table, the translation table accepting input from the control computer to raster the ultrasonic scanner laterally to a direction of travel of the chassis.

9. The device of claim 8, further comprising a suspension interposing the scanner and the translation table.

10. The device of claim 9, wherein the suspension systems provides for at least one axis of rotation of the scanner.

11. The of claim 9, wherein the suspension system is provided with ball casters to prevent damage to the surface when contact with the surface is made by the suspension system.

12. The device of claim 8, wherein the ultrasonic scanning mechanism comprises a plurality of ultrasonic scanners secured to the chassis to scan multiple areas of the surface.

13. The device of claim 8, wherein the self propelled chassis further comprises a tracked chassis.

14. The device of claim 8, further comprising
   a vision system attached to the chassis and having at least one camera directed to the surface, the vision system interfacing with the computer and the computer controlling the chassis to correct deviations in a predetermined path traveled by the chassis over the surface.

15. An automated wing scanning device for operation upon an upper surface of an aircraft wing having a surface skin with a plurality of fasteners thereon connecting the skin to an airframe, the device comprising:
   a track propelled chassis having two tracks, the tracks having rubber treads and a sufficient base area to allow the chassis to operate on a slope of up to at least fifteen degrees when the surface skin is wet;
   a translation table connected to the chassis and providing a suspended carriage that is selectively rastered across the surface skin;
   an ultrasonic scanner secured within the suspended carriage for selectively scanning the wing surface; and
   a control system that controls the chassis to follow a predetermined scan path across the wing surface, controls the translation table to translate the carriage and scanner across the wings surface, and accepts readings from the ultrasonic scanner.

16. The device of claim 15, further comprising a camera mounted to the chassis with a view of the wing surface and interfaced to the control system to allow the control system to correct deviations from the predetermined path on the wing surface.

* * * * *